(12) United States Patent
Kaneko et al.

(10) Patent No.: US 9,023,956 B2
(45) Date of Patent: May 5, 2015

(54) CLATHRATE, CURING AGENT, CURE ACCELERATOR, EPOXY RESIN COMPOSITION, AND EPOXY RESIN COMPOSITION FOR ENCAPSULATION OF SEMICONDUCTOR

(75) Inventors: Masami Kaneko, Ichihara (JP); Kazuo Ono, Ichihara (JP)

(73) Assignee: Nippon Soda Co., Ltd., Tokyo (JP)

( * ) Notice: Subject to any disclaimer, the term of this patent is extended or adjusted under 35 U.S.C. 154(b) by 220 days.

(21) Appl. No.: 13/138,654

(22) PCT Filed: Mar. 15, 2010

(86) PCT No.: PCT/JP2010/001830
§ 371 (c)(1),
(2), (4) Date: Sep. 15, 2011

(87) PCT Pub. No.: WO2010/106780
PCT Pub. Date: Sep. 23, 2010

(65) Prior Publication Data
US 2012/0004377 A1    Jan. 5, 2012

(30) Foreign Application Priority Data

Mar. 17, 2009 (JP) ................................. 2009-065024
Mar. 19, 2009 (JP) ................................. 2009-068786

(51) Int. Cl.
| | | |
|---|---|---|
| *C07D 221/02* | (2006.01) |
| *C07D 233/56* | (2006.01) |
| *C07D 233/58* | (2006.01) |
| *C07D 233/60* | (2006.01) |
| *C07D 233/61* | (2006.01) |
| *C07D 233/64* | (2006.01) |
| *C08G 59/42* | (2006.01) |
| *C08G 59/68* | (2006.01) |
| *H01L 23/29* | (2006.01) |
| *C07D 233/54* | (2006.01) |
| *C08G 59/40* | (2006.01) |
| *C08G 59/70* | (2006.01) |

(52) U.S. Cl.
CPC ............ *H01L 23/293* (2013.01); *C07D 233/60* (2013.01); *C07D 233/61* (2013.01); *C07D 233/56* (2013.01); *C07D 233/64* (2013.01); *C07D 233/58* (2013.01); *C07D 221/02* (2013.01); *C07D 233/54* (2013.01); *C08G 59/4014* (2013.01); *C08G 59/4223* (2013.01); *C08G 59/4007* (2013.01); *C08G 59/70* (2013.01)

(58) Field of Classification Search
None
See application file for complete search history.

(56) References Cited

U.S. PATENT DOCUMENTS

| | | | |
|---|---|---|---|
| 3,746,686 A | 7/1973 | Marshall et al. | |
| 4,072,734 A * | 2/1978 | Nakata et al. ................. | 525/187 |
| 5,153,239 A | 10/1992 | Kitagawa et al. | |
| 2010/0016475 A1* | 1/2010 | Doering et al. ............... | 523/461 |
| 2010/0022744 A1* | 1/2010 | Kaneko et al. ................ | 528/408 |
| 2010/0179250 A1* | 7/2010 | Ono et al. ..................... | 523/455 |

FOREIGN PATENT DOCUMENTS

| | | | |
|---|---|---|---|
| EP | 0 949 286 A1 | 10/1999 | |
| JP | 49-032999 A | 3/1974 | |
| JP | 56-131620 A * | 10/1981 | |
| JP | 61-264016 A | 11/1986 | |
| JP | 04-002638 A | 1/1992 | |
| JP | 04-266922 A | 9/1992 | |
| JP | 05-194711 A | 8/1993 | |
| JP | 06-100662 A | 4/1994 | |
| JP | 6-100662 A * | 4/1994 | |
| JP | 7-330870 A * | 12/1995 | |
| JP | 07-330870 A | 12/1995 | |
| JP | 09-143250 A | 6/1997 | |
| JP | 9-143250 A * | 6/1997 | |
| JP | 10-324826 A | 12/1998 | |
| JP | 11-071449 A | 3/1999 | |
| JP | 2002-020714 A | 1/2002 | |
| JP | 2002-47337 A * | 2/2002 | |
| JP | 2002-047337 A | 2/2002 | |
| JP | 2004-307545 A | 11/2004 | |
| JP | 2005-120222 A | 5/2005 | |
| JP | 2007-39449 A * | 2/2007 | |
| WO | WO 2008/075427 A1 * | 6/2008 | |
| WO | WO 2009/037862 A1 | 3/2009 | |

OTHER PUBLICATIONS

International Search Report mailed Jun. 15, 2010, in PCT/JP2010/001830, 4 pages.
Final Office Action dated Sep. 7, 2012 in copending U.S. Appl. No. 12/733,462.
Du et al., "Bis(4-methylimidazolium) succinate succinic acid solvate," Acta Crystallographica Section E Structure Reports Online, Feb. 25, 2009, 65(3):o607-o608, sup-1-sup-9, XP055099118.
Liu, Zhi-Xiong, "2-Methylimidazolium hydrogen maleate," Acta Crystallographica Section E Structure Reports Online, Feb. 11, 2009, 36(3):o499, sup-1-sup-8, XP055099115.

* cited by examiner

*Primary Examiner* — Robert Sellers
(74) *Attorney, Agent, or Firm* — Foley & Lardner LLP

(57) ABSTRACT

It is an object of the present invention to provide a clathrate that suppresses a curing reaction at low temperature to promote an improvement in storage stability (one-component stability), and can effectively cure a resin by heating treatment. A clathrate suitable for the clathrate is a clathrate containing (b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid; and (b2) at least one selected from the group consisting of an imidazole compound represented by the following formula (I), and 1,8-diazabicyclo[5.4.0]undecene-7, at a molar ratio of 1:1.

2 Claims, No Drawings

US 9,023,956 B2

CLATHRATE, CURING AGENT, CURE ACCELERATOR, EPOXY RESIN COMPOSITION, AND EPOXY RESIN COMPOSITION FOR ENCAPSULATION OF SEMICONDUCTOR

TECHNICAL FIELD

The present invention relates to a novel clathrate, and an epoxy resin composition and an epoxy resin composition for encapsulation of a semiconductor, using the same.

This application is the U.S. National Stage of PCT/JP2010/001830, filed Mar. 15, 2010, which claims priority to Japanese Patent Application No. 2009-065024 filed on Mar. 17, 2009, and Japanese Patent Application No. 2009-068786 filed on Mar. 19, 2009, the content of which is incorporated herein.

BACKGROUND ART

Epoxy resins have excellent mechanical properties and thermal properties, and therefore are widely used in various fields. Imidazole is used as a curing agent for curing such epoxy resins. But, a problem of an epoxy resin-imidazole mixed liquid is that it cannot be used as a one-component type because curing starts early and it is thickened or gelled in long-term storage.

Accordingly, the use of an imidazole acid addition salt in which hydroxybenzoic acid is added to imidazole, as the curing agent (see Patent Document 1), and the use of an inclusion compound of a tetrakisphenol compound (for example, 1,1,2,2-tetrakis(4-hydroxyphenyl)ethane (hereinafter referred to as TEP)) and imidazole as the curing agent (see Patent Documents 2 and 3) are proposed. In addition, the present inventors propose a cured resin composition using an inclusion compound of an isophthalic acid compound and imidazole (see Patent Document 4). But, although these achieve a certain effect, these are not satisfactory yet.

Epoxy resin compositions containing an epoxy resin, a curing agent, a cure accelerator, and other additives are used as encapsulation materials for semiconductor devices, such as transistors, ICs, and LSIs, and electrical components. For the purpose of improving the preservation stability of the epoxy resin compositions, the use of an inclusion compound comprising an imidazole compound or an amine compound as a guest compound and TEP as a host, as the cure accelerator, is proposed (see Patent Document 5). The inclusion of an imidazole compound or an amine compound can promote an improvement in the preservation stability of the encapsulation material at ordinary temperature, compared with a case where these compounds are used alone or in combination. But, it is not sufficiently satisfactory for an encapsulation material composition that addresses the fine specifications of semiconductors which have been significantly advanced in recent years.

In addition, salts of aliphatic divalent carboxylic acids and imidazole compounds are known (see Patent Documents 6 to 10), but all have a content ratio of 1:2.

PRIOR ART DOCUMENTS

Patent Documents

Patent Document 1: Japanese Patent Publication No. 4-2638
Patent Document 2: Japanese Patent Laid-Open No. 11-71449
Patent Document 3: Japanese Patent Laid-Open No. 10-324826
Patent Document 4: International Publication No. WO2008/075427
Patent Document 5: Japanese Patent Laid-Open No. 2004-307545
Patent Document 6: Japanese Patent Laid-Open No. 49-32999
Patent Document 7: Japanese Patent Laid-Open No. 61-264016
Patent Document 8: Japanese Patent Laid-Open No. 6-100662
Patent Document 9: Japanese Patent Laid-Open No. 9-143250
Patent Document 10: Japanese Patent Laid-Open No. 2002-47337

SUMMARY OF THE INVENTION

Object to be Solved by the Invention

It is an object of the present invention to provide a clathrate that suppresses a curing reaction at low temperature to promote an improvement in storage stability (one-component stability), and can effectively cure a resin by heating treatment. In addition, the present invention aims to provide an epoxy resin composition that improves the preservation stability of an encapsulation material, keeps the flowability of the encapsulation material during encapsulation, and achieves an efficient rate of curing of the encapsulation material by heat, in order to address an encapsulation material for a dense semiconductor. In addition, the present invention aims to provide a curable epoxy resin composition that has excellent storage stability and curing properties, in a composition containing an organic solvent, or a composition containing a liquid epoxy resin as a base resin, for which storage stability is particularly required.

Means to Solve the Object

The present inventors have studied diligently to solve the above object, and, as a result, found that the above object can be solved when a clathrate comprising an aliphatic polyvalent carboxylic acid, 5-nitroisophthalic acid, 5-tert-butylisophthalic acid, 5-hydroxyisophthalic acid, isophthalic acid, or benzophenone-4,4'-dicarboxylic acid as a host, and an imidazole compound or 1,8-diazabicyclo[5.4.0]undecene-7 as a guest compound is formed, and it is used as a curing agent and/or a cure accelerator for an epoxy resin, thereby leading to the completion of the present invention.

Specifically, the present invention is

[1] a clathrate containing:

(b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid; and (b2) at least one selected from the group consisting of an imidazole compound represented by formula (I):

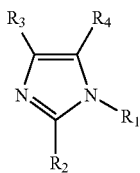

wherein $R_1$ represents a hydrogen atom, a C1-C10 alkyl group, an aryl group, an aralkyl group, or a cyanoethyl group, and $R_2$ to $R_4$ represent a hydrogen atom, a nitro group, a halogen atom, a C1-C20 alkyl group, a C1-C20 alkyl group substituted by a hydroxy group, an aryl group, an aralkyl group, or a C1-C20 acyl group, and 1,8-diazabicyclo[5.4.0]undecene-7, at a molar ratio of 1:1, provided that when (b1) is 5-nitroisophthalic acid, 5-tert-butylisophthalic acid, 5-hydroxyisophthalic acid, isophthalic acid, and benzophenone-4,4'-dicarboxylic acid, (b2) is limited to 1,8-diazabicyclo[5.4.0]undecene-7,

[2] the clathrate according to [1], wherein the aliphatic polyvalent carboxylic acid of component (b1) is an aliphatic divalent to tetravalent carboxylic acid,

[3] the clathrate according to [1] and [2], wherein the aliphatic polyvalent carboxylic acid of the component (b1) is a hydroxy aliphatic polyvalent carboxylic acid,

[4] the clathrate according to any one of [1] to [3], wherein $R_4$ of an imidazole compound represented by formula (I) in component (b2) is a C1-C10 alkyl group substituted by a hydroxy group, and

[5] the clathrate according to any one of [1] to [4], wherein $R_4$ of an imidazole compound represented by formula (I) in the component (b2) is a hydroxymethyl group.

In addition, the present invention relates to

[6] a solid epoxy resin composition containing the following component (A) and component (B):

(A) an epoxy resin; and
(B) a clathrate containing
(b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid, and
(b2) at least one selected from the group consisting of an imidazole compound represented by formula (I):

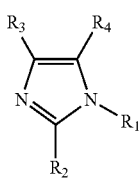

(wherein $R_1$ represents a hydrogen atom, a C1-C10 alkyl group, an aryl group, an aralkyl group, or a cyanoethyl group, and $R_2$ to $R_4$ each represent a hydrogen atom, a nitro group, a halogen atom, a C1-C20 alkyl group, a C1-C20 alkyl group substituted by a hydroxy group, an aryl group, an aralkyl group, or a C1-C20 acyl group), and 1,8-diazabicyclo[5.4.0]undecene-7, at a molar ratio of 1:1, provided that when (b1) is 5-nitroisophthalic acid, 5-tert-butylisophthalic acid, 5-hydroxyisophthalic acid, isophthalic acid, and benzophenone-4,4'-dicarboxylic acid, (b2) is limited to 1,8-diazabicyclo[5.4.0]undecene-7,

[7] the solid epoxy resin composition according to [6], wherein the aliphatic polyvalent carboxylic acid of component (b1) is an aliphatic divalent to tetravalent carboxylic acid,

[8] the solid epoxy resin composition according to [6] or [7], wherein the aliphatic polyvalent carboxylic acid of component (b1) is a hydroxy aliphatic polyvalent carboxylic acid,

[9] the solid epoxy resin composition according to any one of [6] to [8], wherein $R_4$ of an imidazole compound represented by formula (I) in a component (b2) is a C1-C10 alkyl group substituted by a hydroxy group, and

[10] the solid epoxy resin composition according to any one of [6] to [9], wherein $R_4$ of an imidazole compound represented by formula (I) in component (b2) is a hydroxymethyl group.

Further, the present invention relates to

[11] a curing agent or a cure accelerator for an epoxy resin composition, containing a clathrate containing: (b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid; and
(b2) at least one selected from the group consisting of an imidazole compound represented by formula (I):

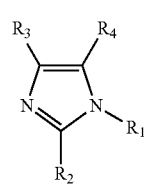

(wherein $R_1$ represents a hydrogen atom, a C1-C10 alkyl group, an aryl group, an aralkyl group, or a cyanoethyl group, and $R_2$ to $R_4$ each represent a hydrogen atom, a nitro group, a halogen atom, a C1-C20 alkyl group, a C1-C20 alkyl group substituted by a hydroxy group, an aryl group, an aralkyl group, or a C1-C20 acyl group), and 1,8-diazabicyclo[5.4.0]undecene-7, at a molar ratio of 1:1, provided that when (b1) is 5-nitroisophthalic acid, 5-tert-butylisophthalic acid, 5-hydroxyisophthalic acid, isophthalic acid, and benzophenone-4,4'-dicarboxylic acid, (b2) is limited to 1,8-diazabicyclo[5.4.0]undecene-7,

[12] the curing agent or the cure accelerator for an epoxy resin composition according to [11], wherein the aliphatic polyvalent carboxylic acid of component (b1) is an aliphatic divalent to tetravalent carboxylic acid,

[13] the curing agent or the cure accelerator for an epoxy resin composition according to [11] or [12], wherein the aliphatic polyvalent carboxylic acid of component (b1) is a hydroxy aliphatic polyvalent carboxylic acid,

[14] the curing agent or the cure accelerator for an epoxy resin composition according to any one of [11] to [13], wherein $R_4$ of an imidazole compound represented by formula (I) in component (b2) is a C1-C10 alkyl group substituted by a hydroxy group, and

[15] the curing agent or the cure accelerator for an epoxy resin composition according to any one of [11] to [14], wherein $R_4$ of the imidazole compound represented by formula (I) in component (b2) is a hydroxymethyl group.

Further, the present invention relates to
[16] a solid epoxy resin composition for encapsulation of a semiconductor, containing the composition according to any one of [6] to [10].

MODE OF CARRYING OUT THE INVENTION (1) New Clathrate

The clathrate of the present invention is not particularly limited as long as it is a clathrate containing:
(b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid; and
(b2) at least one selected from the group consisting of an imidazole compound represented by formula (I):

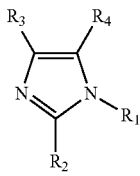

wherein $R_1$ represents a hydrogen atom, a C1-C10 alkyl group, an aryl group, an aralkyl group, or a cyanoethyl group, and $R_2$ to $R_4$ each represent a hydrogen atom, a nitro group, a halogen atom, a C1-C20 alkyl group, a C1-C20 alkyl group substituted by a hydroxy group, an aryl group, an aralkyl group, or a C1-C20 acyl group, and 1,8-diazabicyclo[5.4.0] undecene-7 (hereinafter referred to as DBU),
at a molar ratio of 1:1.

However, when (b1) is 5-nitroisophthalic acid, 5-tert-butylisophthalic acid, 5-hydroxyisophthalic acid, isophthalic acid, and benzophenone-4,4'-dicarboxylic acid, (b2) is limited to 1,8-diazabicyclo[5.4.0]undecene-7.

Here, the "clathrate" refers to a compound in which two or three or more molecules are bonded to each other via a bond other than a covalent bond, more preferably, a crystalline compound in which two or three or more molecules are bonded to each other via a bond other than a covalent bond. An including compound is referred to as a host compound, and an included compound is referred to as a guest compound. In addition, the clathrate as used herein also comprises salts.

(Host Compound)

Here, the aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid of the above component (b1) are host compounds.

The aliphatic polyvalent carboxylic acid includes linear or branched saturated fatty acids, linear or branched unsaturated fatty acids, and cyclic saturated or unsaturated fatty acids. Specific examples thereof can include fumaric acid, 1,3-cyclohexanedicarboxylic acid, trans-1,4-cyclohexanedicarboxylic acid, tartaric acid, succinic acid, malonic acid, maleic acid, citric acid, malic acid, and adipic acid. Aliphatic carboxylic acids having 2 to 4 carboxyl groups and 2 to 10 carbon atoms (not comprising the carbon atoms of the carboxyl groups), or hydroxy aliphatic polyvalent carboxylic acids having 2 to 10 carbon atoms (not comprising the carbon atoms of the carboxyl groups) are preferred. One of these carboxylic acid compounds may be used alone, or two or more of these carboxylic acid compounds may be used in combination.

(Guest Compound)

The guest compound used in the present invention is the component (b2), and is at least one selected from the group consisting of an imidazole compound represented by formula (I) and DBU.

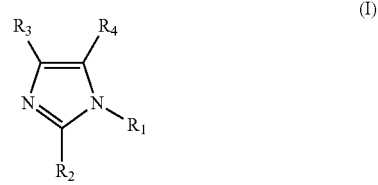

wherein $R_1$ represents a hydrogen atom, a C1-C10 alkyl group, an aryl group, an aralkyl group, or a cyanoethyl group, and $R_2$ to $R_4$ each represent a hydrogen atom, a nitro group, a halogen atom, a C1-C20 alkyl group, a C1-C20 alkyl group substituted by a hydroxy group, an aryl group, an aralkyl group, or a C1-C20 acyl group.

The alkyl group, the aryl group, the aralkyl group, or the acyl group of $R_1$ to $R_4$ may have a substituent. Examples of the substituent can include an alkyl group, a hydroxy group, an alkoxy group, an aryl group, an aralkyl group, and a halogen atom. Examples of the aryl group can include a phenyl group, and examples of the aralkyl group can include a benzyl group.

Examples of the C1-C10 alkyl group of $R_1$ include a methyl group, an ethyl group, a propyl group, an isopropyl group, a cyclopropyl group, a butyl group, an isobutyl group, an s-butyl group, a t-butyl group, a cyclobutyl group, a cyclopropylmethyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 1-ethylbutyl group, a 2-ethylbutyl group, an octyl group, a nonyl group, a decyl group, a hydroxymethyl group and a hydroxyethyl group.

Examples of the C1-C20 alkyl group of $R_2$ to $R_4$ include, in addition to those mentioned as the alkyl group of $R_1$, an undecyl group, a lauryl group, a palmityl group, and a stearyl group.

Examples of the C1-C20 alkyl group substituted by a hydroxy group in $R_2$ to $R_4$ include a hydroxymethyl group or a hydroxyethyl group.

Examples of the C1-C20 acyl group of $R_2$ to $R_4$ include a formyl group, an acetyl group, a propionyl group, a butyryl group, an isobutyryl group, a valeryl group, a pivaloyl group, a hexanoyl group, an octanoyl group, a decanoyl group, a lauroyl group, a myristoyl group, a palmitoyl group, and a stearoyl group.

The aryl group of $R_2$ to $R_4$ means a monocyclic or polycyclic aryl group. Here, the polycyclic aryl group also includes partially saturated groups, in addition to completely unsaturated groups. Examples thereof include C6-10 aryl groups, such as a phenyl group, a naphthyl group, an azulenyl group, an indenyl group, an indanyl group, and a tetralinyl group.

The aralkyl group of $R_2$ to $R_4$ is a group in which the above aryl group and alkyl group are bonded to each other.

Examples of the aralkyl group include C6-10 aryl C1-6 alkyl groups, such as a benzyl group, a phenethyl group, a 3-phenyl-n-propyl group, a 1-phenyl-n-hexyl group, a naphthalene-1-ylmethyl group, a naphthalene-2-ylethyl group, a 1-naphthalene-2-yl-n-propyl group, and an indene-1-ylmethyl group.

Particularly, those in which $R_4$ is a C1-C10 alkyl group substituted by a hydroxy group are preferred. Among them, those in which $R_4$ is a hydroxymethyl group are further preferred.

Specific examples of the imidazole compound include, for example, imidazole, 1-methylimidazole, 2-methylimidazole, 3-methyl imidazole, 4-methylimidazole, 5-methylimidazole, 1-ethylimidazole, 2-ethylimidazole, 3-ethylimidazole, 4-ethylimidazole, 5-ethylimidazole, 1-n-propylimidazole, 2-n-propylimidazole, 1-isopropylimidazole, 2-isopropylimidazole, 1-n-butylimidazole, 2-n-butylimidazole, 1-isobutylimidazole, 2-isobutylimidazole, 2-undecyl-1H-imidazole, 2-heptadecyl-1H-imidazole, 1,2-dimethylimidazole, 1,3-dimethylimidazole, 2,4-dimethylimidazole, 2-ethyl-4-methylimidazole, 1-phenylimidazole, 2-phenyl-1H-imidazole, 4-methyl-2-phenyl-1H-imidazole, 2-phenyl-4-methylimidazole, 1-benzyl-2-methylimidazole, 1-benzyl-2-phenylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 2-phenyl-4,5-dihydroxymethylimidazole, 2-phenyl-4-methyl-5-hydroxymethylimidazole, and 1-cyanoethyl-2-phenyl-4,5-di(2-cyanoethoxy)methylimidazole.

Among these, an imidazole compound that is at least one selected from the group consisting of 2-methylimidazole, 2-ethyl-4-methylimidazole, 2-undecylimidazole, and 2-phenyl-4-methyl-5-hydroxymethylimidazole is more preferred.

In the clathrate of the present invention, it is essential that the molar ratio of the constituting host compound and guest compound is 1:1. The present invention does not comprise those having a molar ratio of 1:2 and the like.

(Method for Producing Clathrate)

The clathrate of the present invention can be obtained by directly mixing, or mixing in a solvent, the above host compound and guest compound.

When a solvent is used, a clathrate can be obtained by adding the above host compound and guest compound to the solvent, then subjecting the mixture to heating treatment or heating and reflux treatment, while stirring the mixture as required, and then precipitating the clathrate. Particularly, the clathrate is more preferably a crystalline compound. The clathrate is not particularly limited as long as it is a precipitated compound, and may comprise a third component, such as a solvent. The third component is preferably 40 mol % or less, more preferably 35 mol % or less, further preferably 20 mol % or less, and particularly preferably 10 mol % or less. Most preferably, the clathrate comprises no third component.

The above host compound and guest compound are dissolved or suspended in a solvent, and preferably, both are dissolved in a solvent. When the above host compound and guest compound are dissolved in a solvent, the total amount of them need not be dissolved in the solvent, and at least a very small portion of them can be dissolved in the solvent. Water, methanol, ethanol, ethyl acetate, methyl acetate, diethyl ether, dimethyl ether, acetone, methyl ethyl ketone, acetonitrile, and the like can be used as the solvent. Particularly, it is preferred to dissolve the host compound and the guest compound in solvents respectively, and then mix the solutions.

The heating treatment is not particularly limited. For example, the mixture can be heated to the range of 40 to 120° C., and is preferably heated to reflux.

The proportion of the above host compound and guest compound added is not particularly limited as long as a clathrate can be formed so that the molar ratio of the host compound and the guest compound in the clathrate is 1:1.

The steps after the above host compound and guest compound are dissolved or suspended in a solvent and the mixture is heated are not particularly limited as long as a solid compound comprising the host compound and the guest compound at a molar ratio of 1:1 can be obtained. For example, after the heating, the solid compound may be precipitated by simply stopping the heating. But, preferably, after the heating, the mixture is allowed to stand overnight at room temperature. In addition, the mixture may be allowed to stand at 5° C. or less, as appropriate, for precipitation. After the solid compound is precipitated, the target compound is obtained, for example, by filtering and drying the solid compound. In addition, a crystalline compound is obtained, depending on the type.

The structure of the obtained clathrate can be confirmed by thermal analysis (TG and DTA), an infrared absorption spectrum (IR), an X-ray diffraction pattern, a solid-state NMR spectrum, and the like. In addition, the composition of the clathrate can be confirmed by thermal analysis, a $^1$H-NMR spectrum, high performance liquid chromatography (HPLC), elementary analysis, and the like.

(2) Epoxy Resin Composition

The epoxy resin composition of the present invention contains the following component (A) and component (B), and is a solid resin composition:

(A) an epoxy resin; and (B) a clathrate containing (b1) at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid, and (b2) at least one selected from the group consisting of an imidazole compound represented by formula (I):

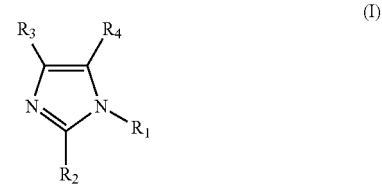

wherein $R_1$ represents a hydrogen atom, a C1-C10 alkyl group, an aryl group, an aralkyl group, or a cyanoethyl group, and $R_2$ to $R_4$ each represent a hydrogen atom, a nitro group, a halogen atom, a C1-C20 alkyl group, a C1-C20-alkyl group substituted by a hydroxy group, an aryl group, an aralkyl group, or a C1-C20 acyl group, and

DBU, at a molar ratio of 1:1.

However, for the clathrate, when (b1) is 5-nitroisophthalic acid, 5-tert-butylisophthalic acid, 5-hydroxyisophthalic acid, isophthalic acid, and benzophenone-4,4'-dicarboxylic acid, (b2) is limited to 1,8-diazabicyclo[5.4.0]undecene-7.

(Epoxy Resin)

As the epoxy resin of the component (A), conventionally known various polyepoxy compounds can be used. Examples thereof can include aromatic glycidyl ether compounds, such as bis(4-hydroxyphenyl)propane diglycidyl ether, bis(4-hydroxy-3,5-dibromophenyl)propane diglycidyl ether, bis(4- hydroxyphenyl)ethane diglycidyl ether, bis(4-hydroxyphenyl)methane diglycidyl ether, resorcinol diglycidyl ether, phloroglucinol triglycidyl ether, trihydroxybiphenyl triglycidyl ether, tetraglycidylbenzophenone, bisresorcinol tetraglycidyl ether, tetramethylbisphenol A diglycidyl ether, bisphenol C diglycidyl ether, bisphenolhexafluoropropane diglycidyl ether, 1,3-bis[1-(2,3-epoxypropoxy)-1-trifluoromethyl-2,2,2-trifluoroethyl]benzene, 1,4-bis[1-(2,3-epoxypropoxy)-1-trifluoromethyl-2,2,2-trifluoromethyl]benzene, 4,4'-bis(2,3-epoxypropoxy)octafluorobiphenyl, and phenol novolak type bisepoxy compounds, alicyclic polyepoxy compounds, such as alicyclic diepoxy acetals, alicyclic diepoxy adipates, alicyclic diepoxy carboxylates, and vinylcyclohexene dioxide, glycidyl ester compounds, such as diglycidyl phthalate, diglycidyl tetrahydrophthalate, diglycidyl hexahydrophthalate, dimethylglycidyl phthalate, dimethylglycidyl hexahydrophthalate, diglycidyl-p-oxybenzoate, diglycidylcyclopentane-1,3-dicarboxylate, and glycidyl esters of dimer acids, glycidylamine compounds, such as diglycidylaniline, diglycidyltoluidine, triglycidylaminophenol, tetraglycidyldiaminodiphenylmethane, and diglycidyltribromoaniline, and heterocyclic epoxy compounds, such as diglycidylhydantoin, glycidylglycidoxyalkylhydantoin, and triglycidyl isocyanurate.

In the epoxy resin composition of the present invention, no liquid epoxy resin is used.

(Clathrate)

The component (B) is a clathrate containing the component (b1) and the component (b2) and is as described above.

The component (b1) is at least one selected from the group consisting of an aliphatic polyvalent carboxylic acid, 5-nitroisophthalic acid, 5-tert-butylisophthalic acid, 5-hydroxyisophthalic acid, isophthalic acid, and benzophenone-4,4'-dicarboxylic acid.

The aliphatic polyvalent carboxylic acid is fumaric acid, 1,3-cyclohexanedicarboxylic acid, trans-1,4-cyclohexanedicarboxylic acid, tartaric acid, succinic acid, malonic acid, maleic acid, citric acid, malic acid, adipic acid or the like, and is preferably an aliphatic carboxylic acid having 2 to 4 carboxyl groups and 2 to 10 carbon atoms (not comprising the carbon atoms of the carboxyl groups), or a hydroxy aliphatic polyvalent carboxylic acid having 2 to 10 carbon atoms (not comprising the carbon atoms of the carboxyl groups). The component (b2) is as described above. Among them, at least one selected from the group consisting of 2-methylimidazole, 2-ethyl-4-methylimidazole, 2-undecylimidazole, 2-phenyl-4-methyl-5-hydroxymethylimidazole, and DBU is particularly preferred for semiconductor encapsulation applications.

The amount of the clathrate used can be similar to the amount of a usual curing agent or cure accelerator used, and is different depending on the curing method. In the case of an addition type curing agent that reacts with epoxy groups and thus the curing agent molecules are always incorporated into the cured resin, the clathrate is usually used so that the included curing agent and/or cure accelerator (guest compound) is about 0.1 to 1.0 mole with respect to 1 mole of epoxy groups, though also depending on the required properties of the resin. In the case of a polymerization type curing agent or a photoinitiation type curing agent that catalytically induces the ring opening of epoxy groups, without the curing agent molecules being incorporated into the resin, to cause a polymerization addition reaction between oligomers, the case of use as a cure accelerator, and the like, 1.0 mole or less of the clathrate with respect to 1 mole of epoxy groups is sufficient. In other words, for the proportion of the component (A) and the component (B), the epoxy resin composition of the present invention contains preferably 0.01 to 3.0 moles, more preferably 0.1 to 1.0 mole, further preferably 0.3 to 1.0 moles, of the component (b2) in the component (B), with respect to 1 mole of the epoxy rings of the epoxy resin that is the component (A). One of the components (B) may be used alone, or two or more of the components (B) may be used in combination.

The average particle diameter D50 of the clathrate of the component (B) is not particularly limited, and is usually in the range of about 0.01 to 80 μm, preferably about 0.01 to 30 μm.

The epoxy resin composition of the present invention can be produced by mixing the component (A) and the component (B). Usually, the component (A) and the component (B) are heated to about 60 to 100° C. and mixed so that a sufficiently mixed state is formed. In the production of the epoxy resin, one-component stability at the temperature at this time is important. The method for producing an epoxy cured resin is not particularly limited as long as it is a method for subjecting the above epoxy resin composition to heating treatment for curing. Usually, the heating temperature of the heating treatment is 60 to 250° C., preferably 100 to 200° C. It is preferred that the epoxy resin composition is cured at such a temperature in a short time.

(Curing Agent or Curing Accelerator)

In the epoxy resin composition of the present invention, the component (B) is used as a curing agent and also as a curing accelerator, as described above.

When the component (B) is a curing agent, the liquid curable epoxy resin composition of the present invention may further comprise a curing accelerator. When the component (B) is a curing accelerator, the liquid curable epoxy resin composition of the present invention may further comprise a curing agent.

The curing agent that may be contained, other than the component (B), is not particularly limited as long as it is a compound that reacts with the epoxy groups in the epoxy resin to cure the epoxy resin. Similarly, the curing accelerator that may be contained, other than the component (B), is not particularly limited as long as it is a compound that promotes the above curing reaction. As such a curing agent or curing accelerator, any can be selected from those commonly used as conventional curing agents or curing accelerators for epoxy resins, and used. Examples thereof include amine compounds, such as aliphatic amines, alicyclic and heterocyclic amines, aromatic amines, and modified amines, imidazole compounds, imidazoline compounds, amide compounds, ester compounds, phenol compounds, alcohol compounds, thiol compounds, ether compounds, thioether compounds, urea compounds, thiourea compounds, Lewis acid compounds, phosphorus compounds, acid anhydride compounds, onium salt compounds, and active silicon compound-aluminum complexes.

Specific examples of the curing agent and the curing accelerator include the following compounds.

Examples of the aliphatic amines include ethylenediamine, trimethylenediamine, triethylenediamine, tetramethylenediamine, hexamethylenediamine, diethylenetriamine, triethylenetetramine, tetraethylenepentamine, dipropylenediamine, dimethylaminopropylamine, diethylaminopropylamine, trimethylhexamethylenediamine, pentanediamine, bis(2-dimethylaminoethyl)ether, pentamethyldiethylenetriamine, alkyl-t-monoamine, 1,4-diazabicyclo(2,2,2)octane (triethylenediamine), N,N,N',N'-tetramethylhexamethylenediamine, N,N,N',N'-tetramethylpropylenediamine, N,N,N',N'-tetramethylethylenediamine, N,N-dimethylcyclohexylamine, dibutylaminopropylamine, dimethylaminoethoxyethoxyethanol, triethanolamine, and dimethylaminohexanol.

Examples of the alicyclic and heterocyclic amines include piperidine, piperazine, menthanediamine, isophoronediamine, methylmorpholine, ethylmorpholine, N,N',N''-tris(dimethylaminopropyl)hexahydro-s-triazine, a 3,9-bis(3-aminopropyl)-2,4,8,10-tetraoxyspiro(5,5)undecane adduct, N-aminoethylpiperazine, trimethylaminoethylpiperazine, bis(4-aminocyclohexyl)methane, N,N'-dimethylpiperazine, and 1,8-diazabicyclo(4.5.0)undecene-7.

Examples of the aromatic amines include o-phenylenediamine, m-phenylenediamine, p-phenylenediamine, diaminodiphenylmethane, diaminodiphenylsulfone, benzylmethylamine, dimethylbenzylamine, m-xylenediamine, pyridine, picoline, and α-methylbenzylmethylamine.

Examples of the modified amines include epoxy compound addition polyamines, Michael addition polyamines, Mannich addition polyamines, thiourea addition polyamines, ketone-blocked polyamines, dicyandiamide, guanidine, organic acid hydrazides, diaminomaleonitrile, aminimides, a boron trifluoride-piperidine complex, and a boron trifluoride-monoethylamine complex.

Examples of the imidazole compounds include imidazole, 1-methylimidazole, 2-methyl imidazole, 3-methylimidazole, 4-methylimidazole, 5-methylimidazole, 1-ethylimidazole, 2-ethylimidazole, 3-ethylimidazole, 4-ethylimidazole, 5-ethylimidazole, 1-n-propylimidazole, 2-n-propylimidazole, 1-isopropylimidazole, 2-isopropylimidazole, 1-n-butylimidazole, 2-n-butylimidazole, 1-isobutylimidazole, 2-isobutylimidazole, 2-undecyl-1H-imidazole, 2-heptadecyl-1H-imidazole, 1,2-dimethylimidazole, 1,3-dimethylimidazole, 2,4-dimethylimidazole, 2-ethyl-4-methylimidazole, 1-phenylimidazole, 2-phenyl-1H-imidazole, 4-methyl-2-phenyl-1H-imidazole, 2-phenyl-4-methylimidazole, 1-benzyl-2-methylimidazole, 1-benzyl-2-phenylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, a 2-phenylimidazole isocyanuric acid adduct, a 2-methylimidazole isocyanuric acid adduct, 2-phenyl-4,5-dihydroxymethylimidazole, 2-phenyl-4-methyl-5-hydroxymethylimidazole, 1-cyanoethyl-2-phenyl-4,5-di(2-cyanoethoxy)methylimidazole, 1-dodecyl-2-methyl-3-benzylimidazolium chloride, and 1-benzyl-2-phenylimidazole hydrochloride.

Examples of the imidazoline compounds include 2-methylimidazoline and 2-phenylimidazoline.

Examples of the amide compounds include polyamides obtained by the condensation of dimer acids and polyamines.

Examples of the ester compounds include active carbonyl compounds, such as aryl and thioaryl esters of carboxylic acids.

For the phenol compounds, the alcohol compounds, the thiol compounds, the ether compounds, and the thioether compounds, examples of phenolic resin curing agents include aralkyl type phenolic resins, such as phenol aralkyl resins and naphthol aralkyl resins, novolak type phenolic resins, such as phenol novolak resins and cresol novolak resins, modified resins thereof, for example, epoxidized or butylated novolak type phenolic resins, dicyclopentadiene-modified phenolic resins, paraxylene-modified phenolic resins, triphenolalkane type phenolic resins, and polyfunctional phenolic resins. In addition, examples of the above compounds include polyol, polymercaptan, polysulfide, 2-(dimethylaminomethylphenol), 2,4,6-tris(dimethylaminomethyl)phenol, and the tri-2-ethylhexyl hydrochloride of 2,4,6-tris(dimethylaminomethyl)phenol.

Examples of the urea compounds, the thiourea compounds, and the Lewis acid compounds include butylated urea, butylated melamine, butylated thiourea, and boron trifluoride.

Examples of the phosphorus compounds include organic phosphine compounds, for example, primary phosphines, such as alkylphosphines, such as ethylphosphine and butylphosphine, and phenylphosphine; secondary phosphines, such as dialkylphosphines, such as dimethylphosphine and dipropylphosphine, diphenylphosphine, and methylethylphosphine; and tertiary phosphines, such as trimethylphosphine, triethylphosphine, and triphenylphosphine.

Examples of the acid anhydride compounds include phthalic anhydride, tetrahydrophthalic anhydride, hexahydrophthalic anhydride, methyltetrahydrophthalic anhydride, methylhexahydrophthalic anhydride, endomethylenetetrahydrophthalic anhydride, methylendomethylenetetrahydrophthalic anhydride, maleic anhydride, tetramethylenemaleic anhydride, trimellitic anhydride, chlorendic anhydride, pyromellitic anhydride, dodecenylsuccinic anhydride, benzophenonetetracarboxylic anhydride, ethylene glycol bis(anhydrotrimellitate), glycerol tris(anhydrotrimellitate), methylcyclohexenetetracarboxylic anhydride, and polyazelaic anhydride.

Examples of the onium salt compounds and the active silicon compound-aluminum complexes include aryldiazonium salts, diaryliodonium salts, triarylsulfonium salts, a triphenylsilanol-aluminum complex, a triphenylmethoxysilane-aluminum complex, a silyl peroxide-aluminum complex, and a triphenylsilanol-tris(salicylaldehydato)aluminum complex.

Particularly, amine compounds, imidazole compounds, and phenol compounds are preferably used as the above curing agent. Among phenol compounds, phenolic resin curing agents are more preferably used.

(Other Additives)

In addition to those described above, various additives, such as a plasticizer, an organic solvent, a reactive diluent, an extender, a filler, a reinforcing agent, a pigment, a flame retardant, a thickening agent, and a release agent, can be mixed in the epoxy resin composition of the present invention, as required. Examples of other additives include silane coupling agents, such as vinyltrimethoxysilane, vinyltriethoxysilane, γ-glycidoxypropyltrimethoxysilane, γ-glycidoxypropyltriethoxysilane, γ-methacryloxypropyltrimethoxysilane, γ-methacryloxypropyltriethoxysilane, γ-aminopropyltrimethoxysilane, γ-aminopropyltriethoxysilane, N-β(aminoethyl)γ-aminopropyltrimethoxysilane, N-β(aminoethyl)γ-aminopropyltriethoxysilane, N-phenyl-γ-aminopropyltrimethoxysilane, N-phenyl-γ-aminopropyltriethoxysilane, γ-mercaptopropyltrimethoxysilane, and γ-mercaptopropyltriethoxysilane; fillers, such as calcium bicarbonate, light calcium carbonate, natural silica, synthetic silica, fused silica, kaolin, clay, titanium oxide, barium sulfate, zinc oxide, aluminum hydroxide, magnesium hydroxide, talc, mica, wollastonite, potassium titanate, aluminum borate, sepiolite, and xonotlite; elastomer modifiers, such as NBRs, polybutadienes, chloroprene rubbers, silicones, crosslinked NBRs, crosslinked BRs, acrylics, core-shell acrylics, urethane rubbers, polyester elastomers, functional group-containing liquid NBRs, liquid polybutadienes, liquid polyesters, liquid polysulfides, modified silicones, and urethane prepolymers; flame retardants, such as hexabromocyclodecane, bis(dibromopropyl)tetrabromobisphenol A, tris(dibromopropyl)isocyanurate, tris(tribromoneopentyl)phosphate, decabromodiphenyl oxide, bis(pentabromo)phenylethane, tris(tribromophenoxy)triazine, ethylenebistetrabromophthalimide, polybromophenylindan, brominated polystyrene, tetrabromobisphenol A polycarbonate, brominated phenylene ethylene oxide, polypentabromobenzyl acrylate, triphenyl phosphate, tricresyl phosphate, trixynyl phosphate, cresyl diphenyl phosphate, xylyl diphenyl phosphate, cresyl bis(di-2,6-xylenyl)phosphate, 2-ethylhexyl diphenyl phosphate, resorcinol bis(diphenyl)phosphate, bisphenol A bis(diphenyl)phosphate, bisphenol A bis(dicresyl)phosphate, resorcinol bis(di-2,6-xylenyl) phosphate, tris(chloroethyl)phosphate, tris(chloropropyl) phosphate, tris(dichloropropyl)phosphate, tris (tribromopropyl)phosphate, diethyl-N,N-bis(2-hydroxyethyl)aminomethyl phosphonate, oxalate anion-treated aluminum hydroxide, nitrate-treated aluminum hydroxide, high temperature hot water-treated aluminum hydroxide, stannic acid surface-treated hydrated metal compounds, nickel compound surface-treated magnesium hydroxide, silicone polymer surface-treated magnesium hydroxide, phlogopite, multilayer surface-treated hydrated metal compounds, and cation polymer-treated magnesium hydroxide; engineering plastics, such as high density polyethylene, polypropylene, polystyrene, polymethyl methacrylate, polyvinyl chloride, nylon 6,6, polyacetal, polyethersulfone, polyetherimide, polybutylene terephthalate, polyetheretherketone, polycarbonate, and polysulfone; plasticizers; diluents, such as n-butyl glycidyl ether, phenyl glycidyl ether, styrene oxide, t-butylphenyl glycidyl ether, dicyclopentadiene diepoxide, phenol, cresol, and t-butylphenol; extenders; reinforcing agents; colorants; thickening agents; and release agents, such as higher fatty acids, higher fatty acid esters, and higher fatty acid calcium, for example, carnauba wax and polyethylene wax. The amount of these additives mixed is not particularly limited, and can be appropriately determined within limits in which the effect of the present invention is obtained.

Further, the epoxy resin composition of the present invention may contain, in addition to the epoxy resin, other resins. Examples of other resins include polyester resins, acrylic resins, silicon resins, and polyurethane resins.

The epoxy resin composition of the present invention can be preferably used for applications for curing epoxy resins, for example, applications, such as epoxy resin-based adhesives, semiconductor encapsulation materials, laminates for printed wiring boards, varnishes, powder paints, casting materials, and inks.

When a curing agent for an epoxy resin or a cure accelerator for an epoxy resin, consisting of the clathrate of the present invention, is mixed in an uncured epoxy resin, thermal stability, which is extremely important in the control of a curing reaction, is significantly improved, compared with a case where only the guest compound (the curing agent and the cure accelerator before inclusion, such as an amine type or an imidazole type) in the curing agent and cure accelerator for an epoxy resin is mixed. In addition, resin compositions containing these clathrates as a curing agent or a cure accelerator have excellent thermal properties. Three properties, stability (one-component stability) at ordinary temperature, thermal stability during heating from ordinary temperature to the desired curing temperature, and curing temperature, are required for the thermal properties of the resin compositions. An uncured epoxy resin in which the clathrate of the present invention is mixed as a curing agent and a cure accelerator is extremely stable (has good one-component stability) at ordinary temperature, but is cured only by heating to a constant temperature equal to or higher than a certain temperature, and quickly gives the desired cured product.

(3) Epoxy Resin Composition for Encapsulation of Semiconductor

An epoxy resin composition for encapsulation of a semiconductor according to the present invention is a solid composition comprising the above component (A) and component (B) that constitute the above epoxy resin composition, and may comprise (D) an inorganic filler, in addition to the component (A) and the component (B).

(D) the inorganic filler of the epoxy resin composition for encapsulation of a semiconductor according to the present invention is not particularly limited. Examples of (D) the inorganic filler include quartz glass, spherical silica obtained by flame fusion, spherical silica produced by a sol-gel method or the like, crystalline silica, alumina, talc, ammonium nitride, silicon nitride, magnesia, and magnesium silicate. These may be used alone, or two or more of these may be used.

In a method for producing the epoxy resin composition for encapsulation of a semiconductor according to the present invention, the epoxy resin composition for encapsulation of a semiconductor can be produced by melting and kneading a mixture consisting of a predetermined amount of the above components and other additives at a temperature and for a time in which gelation does not occur, using, for example, a kneader, a roll, an extruder, or the like, cooling the mixture, then milling the mixture, and molding the mixture again. In addition, in the method for producing the epoxy resin composition for encapsulation of a semiconductor, melting and kneading with heating may be omitted. The produced epoxy resin composition may be solid or liquid, depending on its composition and production method, and is more preferably solid. When a solid epoxy resin composition is used, the content of the inorganic filler is preferably 70 to 95% with respect to the entire epoxy resin composition.

EXAMPLES

Examples will be shown below, but the present invention is not restricted to these Examples in any way.

1) Examples in which an Aliphatic Polyvalent Carboxylic Acid was Used as a Host Compound Synthesis of Clathrates Synthesis Method 1

Examples 1 to 18 Except for Example 11

Fumaric acid (17.41 g, 150 mmol) and 2-methylimidazole (2MZ 12.32 g, 150 mmol) were mixed in 150 ml of methanol. The mixture was stirred and heated to reflux. Then, the heating was stopped for cooling. The mixture was allowed to cool overnight at room temperature, and then, precipitated crystals were filtered and vacuum-dried. It was confirmed by $^1$H-NMR, TG-DTA, and XRD that the obtained fumaric acid-2MZ clathrate was a clathrate having an inclusion ratio of 1:1. Examples 3, 4, 5, 9, and 10, and Comparative Example 2-1 were synthesized by a similar method. Example 7 and Comparative Examples 1-1 and 3-1 were synthesized by a similar method, except that ethyl acetate was used instead of methanol. Examples 2, 6, 8, 12, 14, 15, 16, 17, and 18 were synthesized by a similar method, except that acetone was used instead of methanol. In addition, Example 13 was similarly synthesized with a mixed solvent of 100 ml of acetone and 10 ml of methanol.

Synthesis Method 2

Example 11

Adipic acid (21.92 g, 150 mmol) was dispersed in 150 ml of acetone, and a solution of 2E4MZ (16.52 g, 150 mmol) in 75 ml of acetone was dropped. After the completion of the dropping, the mixture was stirred for 3 hours, while being heated to reflux. Then, the mixture was cooled to room temperature, and precipitated crystals were filtered and vacuum-dried. It was confirmed by $^1$H-NMR, TG-DTA, and XRD that the obtained adipic acid-2E4MZ clathrate was a clathrate having an inclusion ratio of 1:1. Comparative Example 3-1 was similarly synthesized, changing acetone to ethyl acetate. Comparative Example 4-1 was similarly synthesized, changing acetone to methanol.

Production of Epoxy Resins

Using each of the clathrate of Examples 1 to 18 and Comparative Examples 1-1 to 4-1 as a curing catalyst, materials were mixed with a composition shown in Table 1. Then, the mixture was heated and kneaded at 100° C. for 5 minutes, cooled, and then milled to produce an epoxy resin composition for encapsulation of a semiconductor. The mixing amount of each composition in the table is expressed by parts by mass.

Spiral Flow Test

The epoxy resin composition of each Example was tableted to mold tablets. These tablets were injection-molded under the conditions of 175° C. and a pressure of 70 Kgf/cm$^2$ for 3 minutes, using an Archimedean spiral die and a transfer molding machine, and the length of the injection-molded material was measured. For the spiral flow values, the initial value and the value after a lapse of 168 hours at 25° C. were measured. The retention rate (%) was calculated from the values.

The results are shown in Table 1.

Gel Time

A suitable amount of the epoxy resin composition of each Example was placed on a hot plate at 175° C. by a metal spatula, and stirred using the metal spatula. The time when the sample lost stickiness and peeled Off the hot plate, or the time when the sample lost stickiness was measured.

EOCN-1020-55, epoxy equivalent: 191 to 201 (manufactured by Nippon Kayaku Co., Ltd.) was used for the o-cresol novolak epoxy resin. PSM-4261, OH equivalent: 103 (manufactured by Gun Ei Chemical Industry Co., Ltd.) was used for the novolak phenol. TOWAX131 (manufactured by TOA KASEI CO., LTD.) was used for the release agent. LS2940 (manufactured by Shin-Etsu Chemical Co., Ltd.) was used for the coupling agent. Denka FB-940 spherical silica (manufactured by DENKI KAGAKU KOGYO KABUSHIKI KAISHA) was used for the silica.

In the spiral flow test, it is indicated that the larger its value is, the better the flowability is. The spiral flow value can be appropriately selected depending on the situation in which the composition is used. For the retention rate, it is indicated that the larger its value is, the better the preservation stability of the composition is. The gel time is the time until an encapsulation material loses flowability when it is heated at a constant temperature. The gel time is related to curing properties and can be appropriately selected.

From Table 1, the compositions of the present invention have significant flowability and preservation properties, compared with the compositions comprising no clathrate, and have equal or better flowability and preservation properties, compared with the compositions comprising a clathrate comprising TEP as the host, and, at the same time, have suitable and efficient curability.

TABLE 1

| | Example 1 | Example 2 | Example 3 | Example 4 | Example 5 | Example 6 | Example 7 | Example 8 | Comparative Example 1-1 | Comparative Example 1-2 |
|---|---|---|---|---|---|---|---|---|---|---|
| Host | Fumaric acid | 1,3-Cyclohexane-dicarboxylic acid | Trans-1,4-cyclohexane-dicarboxylic acid | Succinic acid | Malonic acid | Maleic acid | Malic acid | Adipic acid | TEP | — |
| Guest | 2MZ | 2MZ | 2MZ | 2MZ | 2MZ | 2MZ | 2MZ | 2MZ | 2MZ | 2MZ |
| Inclusion ratio | 1:1 | 1:1 | 1:1 | 1:1 | 1:1 | 1:1 | 1:1 | 1:1 | 1:2 | — |
| o-Cresol novolak epoxy resin | 100 | 100 | 100 | 100 | 100 | 100 | 100 | 100 | 100 | 100 |
| Novolak phenol | 50 | 50 | 50 | 50 | 50 | 50 | 50 | 50 | 50 | 50 |
| Release agent | 2 | 2 | 2 | 2 | 2 | 2 | 2 | 2 | 2 | 2 |
| Coupling agent | 5 | 5 | 5 | 5 | 5 | 5 | 5 | 5 | 5 | 5 |
| Silica | 900 | 900 | 900 | 900 | 900 | 900 | 900 | 900 | 900 | 900 |
| Clathrate | 4.83 | 6.19 | 6.19 | 4.88 | 4.54 | 4.83 | 5.26 | 5.56 | 6.853 | 2 |
| Spiral flow value (initial value) [cm] | 83.8 | 36.9 | 85.2 | 63.1 | 74.3 | 73.1 | 64.9 | 29.7 | 36.5 | 2.8 |

TABLE 1-continued

| | | | | | | | | | | |
|---|---|---|---|---|---|---|---|---|---|---|
| Spiral flow retention rate % | 94 | 66 | 71 | 65 | 54 | 54 | 71 | 77 | 64 | 57 |
| Gel time [s] | 32.6 | 8.8 | 24.3 | 12.2 | 18.4 | 26.7 | 28.8 | 15.0 | 17.2 | 5.1 |

* 2MZ: 2-methylimidazole
TEP: 1,1,2,2-tetrakis(4-hydroxyphenyl)ethane

| | Example 9 | Example 10 | Example 11 | Comparative Example 2-1 | Comparative Example 2-2 |
|---|---|---|---|---|---|
| Host | Trans-1,4-cyclohexane-dicarboxylic acid | Succinic acid | Adipic acid | TEP | — |
| Guest | 2E4MZ | 2E4MZ | 2E4MZ | 2E4MZ | 2E4MZ |
| Inclusion ratio | 1:1 | 1:1 | 1:1 | 1:2 | — |
| o-Cresol novolak epoxy resin | 100 | 100 | 100 | 100 | 100 |
| Novolak phenol | 50 | 50 | 50 | 50 | 50 |
| Release agent | 2 | 2 | 2 | 2 | 2 |
| Coupling agent | 5 | 5 | 5 | 5 | 50 |
| Silica | 900 | 900 | 900 | 900 | 900 |
| Clathrate | 5.13 | 4.14 | 4.65 | 5.979 | 2 |
| Spiral flow value (initial value) [cm] | 90.2 | 80.0 | 61.4 | 49.1 | 22.4 |
| Spiral flow retention rate % | 82 | 48 | 51 | 67 | 67 |
| Gel time [s] | 27.6 | 27.1 | 23.8 | 19.9 | 11.0 |

* 2E4MZ: 2-ethyl-4-methylimidazole

| | Example 12 | Example 13 | Example 14 | Example 15 | Comparative Example 3-1 | Comparative Example 3-2 |
|---|---|---|---|---|---|---|
| Host | 1,3-Cyclohexane-dicarboxylic acid | Malonic acid | Maleic acid | Citric acid | TEP | — |
| Guest | 2P4MHZ | 2P4MHZ | 2P4MHZ | 2P4MHZ | 2P4MHZ | 2P4MHZ |
| Inclusion ratio | 1:1 | 1:1 | 1:1 | 1:1 | 1:2 | — |
| o-Cresol novolak epoxy resin | 100 | 100 | 100 | 100 | 100 | 100 |
| Novolak phenol | 50 | 50 | 50 | 50 | 50 | 50 |
| Release agent | 2 | 2 | 2 | 2 | 2 | 2 |
| Coupling agent | 5 | 5 | 5 | 5 | 5 | 5 |
| Silica | 900 | 900 | 900 | 900 | 900 | 900 |
| Clathrate | 3.83 | 3.11 | 3.23 | 4.52 | 4.283 | 2 |
| Spiral flow value (initial value) [cm] | 126.0 | 145.8 | 172.5 | 151.4 | 161.3 | 101.2 |
| Spiral flow retention rate % | 62 | 64 | 54 | 102 | 59 | 57 |
| Gel time [s] | 38.1 | 47.1 | 49.5 | 58.8 | 34.2 | 29.1 |

* 2P4MHZ: 2-phenyl-4-methyl-5-hydroxymethylimidazole

| | Example 16 | Example 17 | Example 18 | Comparative Example 4-1 | Comparative Example 4-2 |
|---|---|---|---|---|---|
| Host | 1,3-Cyclohexane-dicarboxylic acid | Trans-1,4-cyclohexane-dicarboxylic acid | Adipic acid | TEP | — |
| Guest | DBU | DBU | DBU | DBU | DBU |
| Inclusion ratio | 1:1 | 1:1 | 1:1 | 1:1 | — |
| o-Cresol novolak epoxy resin | 100 | 100 | 100 | 100 | 100 |
| Novolak phenol | 50 | 50 | 50 | 50 | 50 |
| Release agent | 2 | 2 | 2 | 2 | 2 |
| Coupling agent | 5 | 5 | 5 | 5 | 5 |
| Silica | 900 | 900 | 900 | 900 | 900 |
| Clathrate | 4.26 | 4.26 | 3.92 | 7.14 | 2 |
| Spiral flow value (initial value) [cm] | 91.9 | 90.4 | 94.3 | 105.6 | 73.6 |

| | | | TABLE 1-continued | | |
|---|---|---|---|---|---|
| Spiral flow retention rate % | 59 | 76 | 73 | 76 | 68 |
| Gel time [s] | 30.7 | 34.0 | 33.6 | 45.2 | 21.0 |

* DBU: 1,8-diazabicyclo[5.4.0]undecene-7

Solvent-Based Epoxy Resins

For the clathrates of Examples 1, 2, 3, and 8, the concentration of imidazole dissolved in methyl ethyl ketone (MEK) is shown in Table 2. According to this, it is seen that the clathrates of the present invention have lower concentration, compared with the cases of TEP and without inclusion, and are preferred for a one-component epoxy resin composition for which storage stability is required.

The dissolved concentration was measured as follows.

A suitable amount of a sample was added to 4 ml of MEK, and the mixture was shaken at 25° C. The sample was added until the sample was not dissolved. The sample liquid was filtered by a 0.2 μm filter, and the imidazole concentration (mg/L) in the solution was obtained by HPLC. (analysis column: Finepak SIL C18S manufactured by JASCO Corporation, mobile phase: aqueous sodium phosphate solution/methanol=60/40)

TABLE 2

| Host | Fumaric acid | 1,3-Cyclohexane-dicarboxylic acid | Trans-1,4-cyclohexane-dicarboxylic acid | Adipic acid | TEP | — |
|---|---|---|---|---|---|---|
| Guest | 2 MZ | 2 MZ | 2 MZ | 2 MZ | 2 MZ | 2 MZ |
| Imidazole concentration ppm | 1.67 | 598.97 | 59.55 | 1024.71 | 6519.13 | 43372.5 |
| Imidazole content % | 41.4 | 32.3 | 32.3 | 36.0 | 29.2 | 100 |

2) Examples in which 5-Nitroisophthalic Acid, 5-Tert-Butylisophthalic Acid, 5-Hydroxyisophthalic Acid, Isophthalic Acid, and Benzophenone-4,4'-Dicarboxylic Acid were Used as a Host Compound Synthesis of Clathrates Example 19

5-Nitroisophthalic acid (42.2 g, 200 mmol) was added to 600 ml of methanol. While the mixture was stirred, a solution of DBU (36.5 g, 240 mmol) in 200 ml of methanol was dropped therein. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained 5-nitroisophthalic acid-DBU clathrate was a clathrate having an inclusion ratio of 1:1.

Example 20

5-Tert-butylisophthalic acid (44.5 g, 200 mmol) was added to 700 ml of acetone. While the mixture was stirred, a solution of DBU (30.5 g, 200 mmol) in 100 ml of acetone was dropped therein. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained 5-tert-butylisophthalic acid-DBU clathrate was a clathrate having an inclusion ratio of 1:1.

Example 21

5-Hydroxyisophthalic acid (9.1 g, 50 mmol) was added to 50 ml of methanol. While the mixture was heated and stirred, DBU (7.6 g, 50 mmol) was dropped therein. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained 5-hydroxyisophthalic acid-DBU clathrate was a clathrate having an inclusion ratio of 1:1.

Example 22

Isophthalic acid (33.2 g, 200 mmol) was added to 400 ml of acetone. While the mixture was stirred, a solution of DBU (33.5 g, 220 mmol) in 200 ml of acetone was dropped therein. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained isophthalic acid-DBU clathrate was a clathrate having an inclusion ratio of 1:1.

Example 23

Benzophenone-4,4'-dicarboxylic acid (4 g, 14.8 mmol) and DBU (2.25 g, 14.8 mmol) were added to 30 ml of ethyl acetate, and the mixture was stirred. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained benzophenone-4,4'-dicarboxylic acid-DBU clathrate was a clathrate having an inclusion ratio of 1:1.

Comparative Example 5

TEP (4.0 g, 10 mmol) was added to 50 ml of methanol, and the mixture was stirred. While the mixture was heated to reflux, a solution of DBU (3.7 g, 24 mmol) in 30 ml of methanol was dropped therein. Then, the mixture was heated to reflux for 5 hours. The heating was stopped for cooling. The mixture was allowed to cool overnight at room temperature, and then, precipitated crystals were filtered and vacuum-dried. It was confirmed by $^1$H-NMR, TG-DTA, and XRD that the obtained TEP-DBU clathrate was a clathrate having an inclusion ratio of 1:1.

Test Examples

Production of Epoxy Resins

Using each of the clathrates of Examples 19 to 24 and Comparative Examples 5 and 6 as a curing catalyst, materials were mixed with a composition shown in Table 3. Then, the mixture was heated and kneaded at 100° C. for 5 minutes, cooled, and then milled to produce an epoxy resin composition for encapsulation of a semiconductor. The mixing amount of each composition in the table is expressed by parts by mass.

Spiral Flow Test

The epoxy resin composition of each Example was tableted to mold tablets. These tablets were injection-molded under the conditions of 175° C. and a pressure of 70 Kgf/cm² for 3 minutes, using an Archimedean spiral die and a transfer molding machine, and the length of the injection-molded material was measured. For the spiral flow values, the initial value and the value after a lapse of 168 hours at 25° C. were measured. The retention rate (%) was calculated from the values.

The results are shown in Table 3.

Gel Time

A suitable amount of the epoxy resin composition of each Example was placed on a hot plate at 175° C. by a metal spatula, and stirred using the metal spatula. The time when the sample lost stickiness and peeled off the hot plate, or the time when the sample lost stickiness was measured.

EOCN-1020-55, epoxy equivalent: 191 to 201 (manufactured by Nippon Kayaku Co., Ltd.) was used for the o-cresol novolak epoxy resin. PSM-4261, OH equivalent: 103 (manufactured by Gun Ei Chemical Industry Co., Ltd.) was used for the novolak phenol. TOWAX131 (manufactured by TOA KASEI CO., LTD.) was used for the release agent. LS2940 (manufactured by Shin-Etsu Chemical Co., Ltd.) was used for the coupling agent. Denka FB-940 spherical silica (manufactured by DENKI KAGAKU KOGYO KABUSHIKI KAISHA) was used for the silica.

In the spiral flow test, it is indicated that the larger its value is, the better the flowability is. The spiral flow value can be appropriately selected depending on the situation in which the composition is used. For the retention rate after 168 hours, it is indicated that the larger its value is, the better the preservation stability of the composition is. The gel time is the time until an encapsulation material loses flowability when it is heated at a constant temperature. The gel time is related to curing properties and can be appropriately selected.

From Table 3, the compositions of the present invention have significant flowability and preservation properties, compared with the compositions comprising no clathrate, and have equal or better flowability and preservation properties, compared with the compositions comprising a clathrate comprising TEP as the host, and, at the same time, have suitable and efficient curability.

|  | Example 19 | Example 20 | Example 21 | Example 22 | Example 23 | Comparative Example 5 | Comparative Example 6 |
|---|---|---|---|---|---|---|---|
| Host | 5-Nitro-isophthalic acid | 5-Tert-butyl-isophthalic acid | 5-Hydroxy-isophthalic acid | Isophthalic acid | Benzophenone-4,4'-dicarboxylic acid | TEP | — |
| Guest | DBU | DBU | DBU | DBU | DBU | DBU | DBU |
| Inclusion ratio | 1:1 | 1:1 | 1:1 | 1:1 | 1:1 | 1:1 | — |
| o-Cresol novolak epoxy resin | 100 | 100 | 100 | 100 | 100 | 100 | 100 |
| Novolak phenol | 50 | 50 | 50 | 50 | 50 | 50 | 50 |
| Release agent | 2 | 2 | 2 | 2 | 2 | 2 | 2 |
| Coupling agent | 5 | 5 | 5 | 5 | 5 | 5 | 5 |
| Silica | 900 | 900 | 900 | 900 | 900 | 900 | 900 |
| Clathrate | 4.77 | 4.91 | 4.39 | 4.182 | 5.55 | 7.23 | 2 |
| Spiral flow value (initial value) [cm] | 114.0 | 118.0 | 120.2 | 108.5 | 112.1 | 105.6 | 73.6 |
| Spiral flow value retention rate % | 104 | 81 | 90 | 58 | 97 | 76 | 68 |
| Gel time [s] | — | 38.2 | 53.9 | 36.7 | 44.6 | 56.9 | 27.8 |

TEP: 1,1,2,2-tetrakis(4-hydroxyphenyl)ethane
DBU: 1,8-diazabicyclo[5.4.0]undecene-7

INDUSTRIAL APPLICABILITY

The new clathrate of the present invention can provide a curing agent and a cure accelerator that provide a resin composition having excellent storage stability and can effectively cure a resin. In addition, the new clathrate of the present invention can provide a solid epoxy resin composition for encapsulation of a semiconductor in which preservation stability and flowability are maintained and which has efficient curability and can address a dense semiconductor circuit.

The invention claimed is:

1. A clathrate containing:
(b1) at least one selected from the group consisting of
5-nitroisophthalic acid,
5-tert-butylisophthalic acid,
and
benzophenone-4,4'-dicarboxylic acid; and
(b2) 1,8-diazabicyclo[5.4.0]undecene-7,
at a molar ratio of 1:1.

2. A curing agent or a cure accelerator for a solid epoxy resin composition, containing a clathrate containing:
(b1) at least one selected from the group consisting of
5-nitroisophthalic acid,
5-tert-butylisophthalic acid,
and
benzophenone-4,4'-dicarboxylic acid; and
(b2) 1,8-diazabicyclo[5.4.0]undecene-7,
at a molar ratio of 1:1.

* * * * *